United States Patent
Ahuja et al.

(10) Patent No.: US 10,558,695 B2
(45) Date of Patent: Feb. 11, 2020

(54) WEATHER-BASED NATURAL LANGUAGE TEXT PROCESSING

(71) Applicant: INTERNATIONAL BUSINESS MACHINES CORPORATION, Armonk, NY (US)

(72) Inventors: Shilpi Ahuja, San Jose, CA (US); Sheng Hua Bao, San Jose, CA (US); Rashmi Gangadharaiah, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/607,694

(22) Filed: May 30, 2017

(65) Prior Publication Data
US 2018/0349326 A1 Dec. 6, 2018

(51) Int. Cl.
G06F 17/27 (2006.01)
G06F 16/34 (2019.01)
G06F 19/00 (2018.01)

(52) U.S. Cl.
CPC ........ *G06F 16/345* (2019.01); *G06F 17/2745* (2013.01); *G06F 17/2785* (2013.01); *G06F 19/30* (2013.01); *G06F 17/271* (2013.01)

(58) Field of Classification Search
CPC combination set(s) only.
See application file for complete search history.

(56) References Cited

U.S. PATENT DOCUMENTS 6,199,034 B1 3/2001 Wical
6,434,524 B1 8/2002 Weber
6,487,545 B1 11/2002 Wical
(Continued)

FOREIGN PATENT DOCUMENTS

CN 105049500 A 11/2015
WO 0068854 A2 11/2000
(Continued)

OTHER PUBLICATIONS

Accuweather, "Local Weather from AccuWeather.com—Superior Accuracy", http://www.accuweather.com/, © 2017 AccuWeather, Inc. All Rights Reserved. AccuWeather.com is a registered trademark of AccuWeather, Inc., printed Feb. 24, 2017, pp. 1-5.
(Continued)

*Primary Examiner* — Vu B Hang
(74) *Attorney, Agent, or Firm* — Jordan T. Schiller (57) ABSTRACT

Relationship extraction between descriptors in one or more lists of weather condition descriptors, and adverse event descriptors within unstructured data sources using natural language processing. Medical condition descriptor may be a descriptor that may be used to further extract relationships between weather condition descriptors and adverse event descriptors. A data object is generated, according to a data model, based on the extracted relationships between the descriptors. A set of candidate unstructured documents containing the extracted relationship between the descriptors is retrieved and filtered by selecting unstructured documents that include a precautionary measure descriptor. The filtered precautionary measure descriptors are presented to a user in a summarized message to a user device.

19 Claims, 6 Drawing Sheets

(56) References Cited

U.S. PATENT DOCUMENTS

| | | | |
|---|---|---|---|
| 6,498,987 | B1 | 12/2002 | Kelly et al. |
| 6,590,529 | B2 | 7/2003 | Schwoegler |
| 7,212,922 | B1 | 5/2007 | Longacre et al. |
| 7,739,104 | B2 | 6/2010 | Berkan et al. |
| 7,872,574 | B2 | 1/2011 | Betts et al. |
| 8,812,298 | B1 | 8/2014 | Wolfram et al. |
| 9,575,963 | B2 | 2/2017 | Pasupalak et al. |
| 9,760,642 | B2 * | 9/2017 | Bahrami ............. G06F 17/2705 |
| 2001/0003214 | A1 * | 6/2001 | Shastri ............... H04N 7/17318 725/109 |
| 2001/0039503 | A1 | 11/2001 | Chan et al. |
| 2007/0088553 | A1 | 4/2007 | Johnson |
| 2007/0124144 | A1 | 5/2007 | Johnson |
| 2011/0221671 | A1 | 9/2011 | King, III et al. |
| 2011/0231385 | A1 * | 9/2011 | Wang .................... G06F 16/951 707/709 |
| 2015/0066479 | A1 | 3/2015 | Pasupalak et al. |
| 2015/0261773 | A1 * | 9/2015 | Walid .................... G06F 16/951 707/769 |
| 2017/0308672 | A1 | 10/2017 | Martin et al. |

FOREIGN PATENT DOCUMENTS

| | | | |
|---|---|---|---|
| WO | 2016037055 | A1 | 3/2016 |
| WO | 2017152636 | A1 | 9/2017 |

OTHER PUBLICATIONS

Bach et al., "A Review of Relation Extraction", https://www.researchgate.net/publication/265006408_A_Review_of_Relation_Extraction, May 2011, Language Technologies Institute School of Computer Science, Canergie Mellon University, pp. 1-15.

Bates, et al., "Detecting Adverse Events Using Information Technology", The Practice of Informatics JAMIA, Review Paper, Journal of the American Medical Information Association, vol. 10, No. 2, Mar./Apr. 2003, pp. 115-128.

Campos, et al., "Biomedical Named Entity Recognition: A Survey of Machine-Learning Tools", Biomedical Named Entity Recognition: A Survey of Machine-Learning Tools, Chapter 8, Text Mining, http://dx.doi.org/10.5772/51066, © 2012 Campos et al.; licensee InTech. (best date available) pp. 175-195.

Das, et al., "A Survey on Automatic Text Summarization", Language Technologies Institute Carnegie Mellon University, (fdipanjan, afmg)@cs.cmu.edu, Nov. 21, 2017, pp. 1-31.

diabetes.co.uk, "Diabetes and Exercise", © 2017, Diabetes Digital Media Ltd., http://www.diabetes.co.uk/exercise-for-diabetics.html, printed on Feb. 23, 2017, pp. 1-7.

IBM News Room, "The Weather Company to Deliver Crucial Weather Data for Safety and Resource Management Solutions to Underserved Areas Around the World", http://www-03.ibm.com/press/us/en/pressrelease/50218.wss, Atlanta, GA, Jul. 21, 2016, pp. 1-3.

IBM News Room, "IBM Watson Ushers in a New Era of Data-Driven Discoveries", https://www-03.ibm.com/press/us/en/pressrelease/44697mss, New York, N.Y., Aug. 28, 2014, pp. 1-4.

IBM Watson Health, "Cognitive systems and the future of healthcare", https://www.ibm.com/watson/health/, printed on Feb. 23, 2017, pp. 1-16.

Wang, et al., "SideEffectPTM: An Unsupervised Topic Model to Mine Adverse Drug Reactions from Health Forums", BCB '14 Proceedings of the 5th ACM Conference on Bioinformatics, Computational Biology, and Health Informatics pp. 321-330, Newport Beach, California—Sep. 20-23, 2014, ACM New York, NY, USA © 2014.

The Weather Channel, "National and Local Weather Forecast, Hurricane, Radar and Report", https://weather.com/, © 2017 The Weather Company, LLC, printed Feb. 23, 2017, pp. 1-4.

Virginia Department of Emergency Management, "Take Precautions in Extreme Cold Weather", http://www.montva.com/filestorage/16277/16344/16657/2838/10183/20140123_nra.pdf, printed on Feb. 24, 2017, pp. 1-2.

Mell et al., "The NIST Definition of Cloud Computing," National Institute of Standards and Technology, U.S. Department of Commerce, Special Publication 800-145, Sep. 2011, pp. 1-7.

IBM: List of IBM Patents or Patent Applications Treated As Related (Appendix P), Nov. 30, 2017, pp. 1-2.

Ahuja et al., U.S. Appl. No. 15/827,313, filed Nov. 30, 2017, titled "Weather-Based Natural Language Text Processing," pp. 1-45.

IBM: List of IBM Patents or Patent Applications Treated as Related (Appendix P), Sep. 16, 2019, pp. 1-2.

Ahuja et al., "Weather-Based Natural Language Text Processing," Application and Drawings, filed Jun. 28, 2019, 45 pages, U.S. Appl. No. 16/456,549.

* cited by examiner

WEATHER-BASED NATURAL LANGUAGE TEXT PROCESSING

BACKGROUND

The present disclosure relates generally to the integration of personal health and general or real-time weather information to provide weather-based precautionary measures output to an end user.

Unstructured text data sources, such as medical journals, weather records, news reports, etc., contain a vast amount of information, including words that describe weather conditions, medical conditions, events, and actions. This information is embodied in electronically stored unstructured text documents. Identifying relationships between various entities in these documents can be achieved by improvements to the computing technology that stores and processes this information.

BRIEF SUMMARY

Embodiments of the present invention may be practiced as a method, a computer program product, and a system.

According to an embodiment, a method for performing electronic natural language processing on unstructured data, extracts relationships between descriptors stored in one or more lists of weather condition descriptors and adverse event descriptors. The method generates a data object according to a data model, based on the extracted relationships between the descriptors, and retrieves a set of candidate unstructured documents that include instances of an adverse event descriptor and a related weather condition descriptor. The method filters the retrieved set of candidate unstructured documents by selecting candidate unstructured documents that include a precautionary measure descriptor.

According to another embodiment, a computer program product for performing electronic natural language processing on unstructured data, includes a non-transitory tangible storage device. The storage device embodies program code that is executable by a processor of a computer to perform a method. The method extracts relationships between descriptors stored in one or more lists of weather condition descriptors and adverse event descriptors. The method generates a data object according to a data model, based on the extracted relationships between the descriptors, and retrieves a set of candidate unstructured documents that include instances of an adverse event descriptor and a related weather condition descriptor. The method filters the retrieved set of candidate unstructured documents by selecting candidate unstructured documents that include a precautionary measure descriptor.

According to another embodiment, a system for performing electronic natural language processing on unstructured data, includes one or more computer devices each having one or more processors and one or more tangible storage devices. The one or more storage devices embody a program. The program has a set of program instructions for execution by the one or more processors. The program instructions include instructions for extracting relationships between descriptors stored in one or more lists of weather condition descriptors and adverse event descriptors. The program instructions generate a data object according to a data model, based on the extracted relationships between the descriptors, and retrieve a set of candidate unstructured documents that include instances of an adverse event descriptor and a related weather condition descriptor. The program instructions filter the retrieved set of candidate unstructured documents by selecting candidate unstructured documents that include a precautionary measure descriptor.

BRIEF DESCRIPTION OF THE DRAWINGS

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Embodiments of the present invention disclose a method, a computer program product, and a system for providing personalized precautionary measures to a user based on weather data and optionally, a user's personal context information.

Weather is known to have a profound impact on the human body. Adverse weather events, such as severe cold or severe heat, can cause illness or even death. However, the link between weather events or weather conditions, and adverse medical conditions or adverse medical events, is not always well understood. Scientists and researchers regularly conduct studies and experiments, and publish their results. However, the volume of this information is so high that no single medical professional, or no single medical institution, can possibly gain comprehensive insights from these document sources that can lead to actionable knowledge.

Merely storing this ocean of information on a conventional computer, and merely performing conventional search and processing on it, are not enough to solve the problem of information overload, and the problem of a lack of actionable knowledge. Medical research results are routinely stored in digitized form, and widely circulated over computing networks, such as the internet. Although these medical documents are searchable, gaining insights from them, based on the totality of the knowledge they represent, remains a significant and complex technological challenge. Information and insights potentially exist in these documents, but they are not ascertainable because current computing technology is inadequate in helping humans gain this actionable knowledge. These ordinary computing systems are entirely deficient in addressing this problem. Therefore, new and significantly improved computing technology (including methods and system) are required to address this very serious deficiency in the prior art of computing technology and information processing.

Embodiments of the invention address these technological challenges by allowing for a personalized precautionary measure recommendation system that can provide a user with relevant and practical tailored precautionary measures that, if heeded, may reduce the chances of an adverse medical event.

Figure 1:
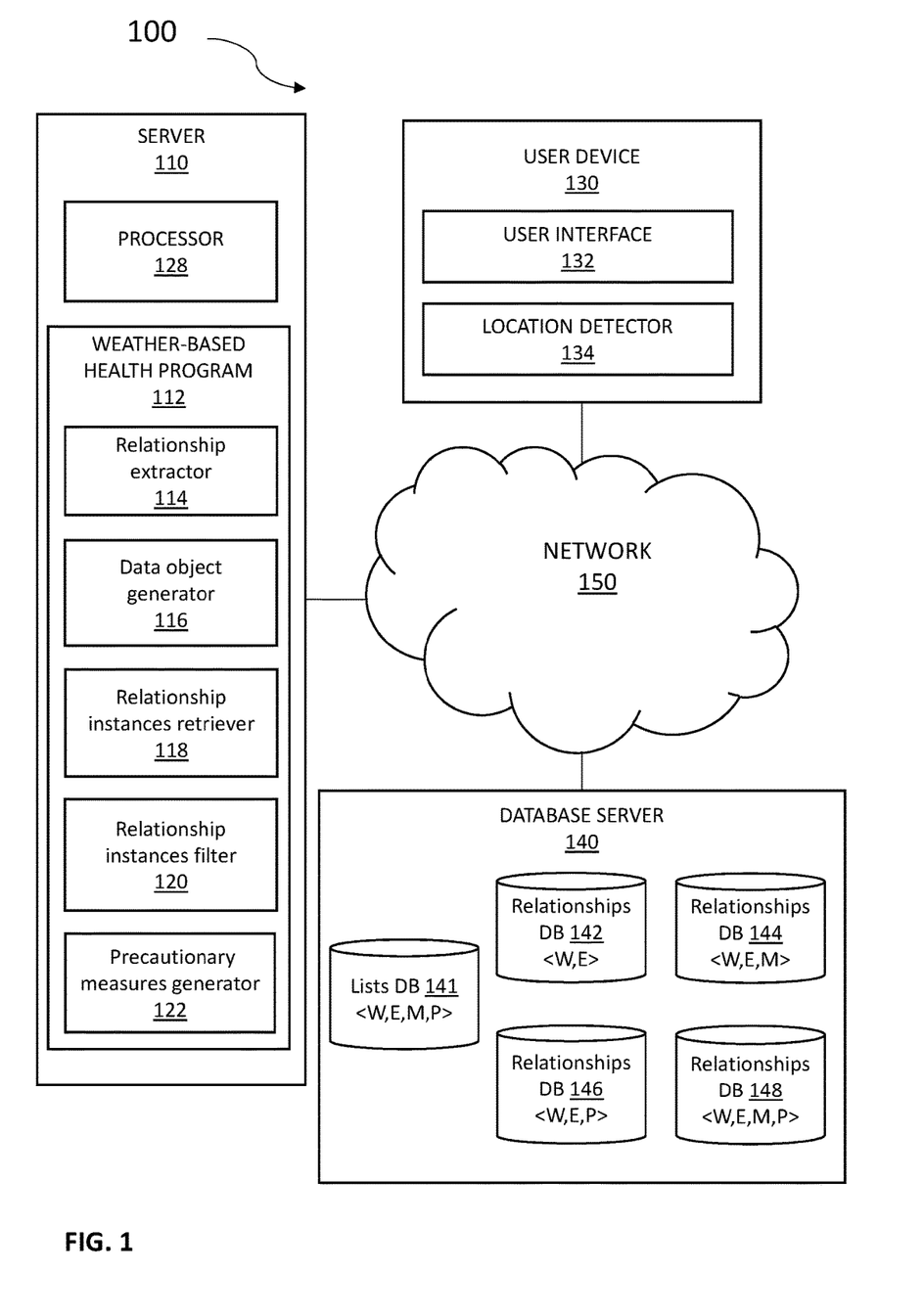
FIG. 1 illustrates a computing environment, in accordance with an embodiment of the present invention.

FIG. 1 is a functional block diagram of a computing environment 100, according to an embodiment of the present invention. Computing environment 100 includes database server 140, server 110, and user device 130 all connected via network 150. The setup in FIG. 1 represents an example embodiment configuration for the present invention, and is not limited to the depicted setup in order to derive benefit from the present invention.

In the example embodiment, database server 140 comprises lists database 141, relationships database 142, relationships database 144, relationships database 146, and relationships database 148 and may be a laptop computer, tablet computer, netbook computer, personal computer (PC), a desktop computer, a personal digital assistant (PDA), a smart phone, or any programmable electronic device capable of communicating with server 110 and user device 130 via network 150. While database server 140 is shown as a single device, in other embodiments, database server 140 may be comprised of a cluster or plurality of computing devices, working together or working separately.

In the example embodiment, lists database 141 includes categorized lists of extracted spans of electronic text, known as descriptors, which comprise words or phrases associated with one or more of the following elements: a weather condition <W>, an adverse event <E>, a medical condition <M>, or a precautionary measure <P>. Relationships database 142, relationships database 144, relationships database 146, and relationships database 148 (the "Relationships Databases") include data objects for extracted relationships between various elements, as further detailed below. Adverse event detectors and weather condition annotators from unstructured text are already known in the art, and as such assist in building lists database 141 and the Relationships Databases. Examples of unstructured text may include online and offline journal articles, blogs, discussions, corpora of data, personal health records, weather databases, medical encyclopedias, peer-reviewed data journals, online data and the like, all of which may be gathered by crawling the world wide web, accessing alternative databases and/or locations by a link or destination path.

In the exemplary embodiment, relationships database 142 comprises extracted relationships between weather condition descriptors <W> and adverse events descriptors <E>. Relationships database 144 comprises extracted relationships between weather condition descriptors <W>, adverse event descriptors <E>, and medical condition descriptors <M>. Relationships database 146 comprises extracted relationships between weather condition descriptors <W>, adverse event descriptors <E>, and precautionary measures descriptors <P>. Relationships database 148 comprises extracted relationships between weather condition descriptors <W>, adverse event descriptors <E>, medical condition descriptors <M>, and precautionary measures descriptors <P>.

In the example embodiment, lists database 141 and the Relationship Databases are built, or configured, prior to the execution of weather-based health program 112. For example, lists database 141 may contain lists of stored data comprising: a span of electronic text representing words or phrases constituting weather condition descriptors <W>; adverse event descriptors <E>; medical condition descriptors <M>; and precautionary measures descriptors <P>. A list of weather condition descriptors may comprise a list of 500 words or phrases that describe the weather, represented as $<W_{1-500}>$, such as hot, sunny, heavy chance of rain, freezing, snowing, etc. A list of adverse event descriptors may comprise a list of 1000 words or phrases that describe an adverse event, represented as $<E_{1-1000}>$, such as dehydration, fainting, rapid heart rate, increased adrenaline rush, etc. A list of medical condition descriptors may comprise a list of 3000 words or phrases that describe a medical condition, represented as $<M_{1-3000}>$, such as diabetes, heart disease, influenza, etc. A list of precautionary measure descriptors may comprise a list of 1500 words or phrases that describe a precautionary measure to be taken, represented as $<P_{1-1500}>$, such as wear a coat, drink fluids, do not shovel snow, etc.

Relationships database 142 may contain stored extracted relationships, or data objects, between corresponding spans of electronic text representing weather condition descriptors and adverse event descriptors, represented as $<W_{number}, E_{number}>$. In the exemplary embodiment, if the weather descriptor "hot" appears as the $35^{th}$ word under weather descriptor words or phrases in lists database 141, and event descriptor "dehydration" appears as the $100^{th}$ word under adverse event descriptor words or phrases in lists database 141, then this relationship, as reflected in the data object, may be represented as $<W_{35}, E_{100}>$ within relationships database 142.

Relationships database 144 may contain stored extracted relationships, as represented by data objects, between corresponding spans of electronic text representing weather condition descriptors, adverse event descriptors, and medical condition descriptors, represented as $<W_{number}, E_{number}, M_{number}>$. In such an embodiment, if the weather descriptor "hot" appears as the $35^{th}$ word under weather descriptor words or phrases in lists database 141, event descriptor "dehydration" appears as the $100^{th}$ word under adverse event descriptor words or phrases in lists database 141, and medical condition descriptor "high blood pressure" appears as the $50^{th}$ word under medical condition descriptor words or phrases in lists database 141, then this relationship may be represented as $<W_{35}, E_{100}, M_{50}>$ within relationships database 144. In other embodiments, the relationship databases may be configured in any other way.

Relationships database 146 may contain stored extracted relationships, represented as data objects, between corresponding spans of electronic text representing weather condition descriptors, adverse event descriptors, and precautionary measures descriptors, represented as $<W_{number}, E_{number}, P_{number}>$. In the exemplary embodiment, if the weather descriptor "hot" appears as the $35^{th}$ word under weather descriptor words or phrases in lists database 141, event descriptor "dehydration" appears as the $100^{th}$ word under adverse event descriptor words or phrases in lists database 141, and precautionary measures descriptor "drink fluids" appears as the $300^{th}$ word or phrase under precautionary measures descriptor words or phrases in lists database 141, then this relationship may be represented as $<W_{35}, E_{100}, P_{300}>$ within relationships database 146. In other embodiments, the relationship databases may be configured in any other way.

Relationships database 148 may contain stored extracted relationships, represented as data objects, between corresponding spans of electronic text representing weather condition descriptors, adverse event descriptors, precautionary measures descriptors, and medical condition descriptors, represented as $<W_{number}, E_{number}, P_{number}, M_{number}>$. In the exemplary embodiment, if the weather descriptor "hot" appears as the $35^{th}$ word under weather descriptor words or phrases in lists database 141, event descriptor "dehydration"

appears as the 100$^{th}$ word under adverse event descriptor words or phrases in lists database 141, precautionary measures descriptor "drink fluids" appears as the 300$^{th}$ word or phrase under precautionary measures descriptor words or phrases in lists database 141, and medical condition descriptor "high blood pressure" appears as the 50$^{th}$ word or phrase under medical condition descriptor words or phrases in lists database 141, then this relationship may be represented as <$W_{35}$, $E_{100}$, $P_{300}$, $M_{50}$> within relationships database 148. In other embodiments, the relationship databases may be configured in any other way.

Server 110, in the example embodiment, may be a laptop computer, tablet computer, netbook computer, personal computer (PC), a desktop computer, a personal digital assistant (PDA), a smart phone, or any programmable electronic device capable of receiving and sending data to and from other computing devices. While server 110 is shown as a single device, in other embodiments, server 110 may be comprised of a cluster or plurality of computing devices, working together or working separately. In the example embodiment, server 110 includes processor 128, and weather-based health program 112 which is stored on a storage device of server 110. Weather-based health program 112 contains instruction sets which may be described using a set of functional modules. Processor 128 executes weather-based health program's 112 instruction sets.

Weather-based health program 112 is a computer program configured to extract and correlate data and to provide precautionary measures output data to a user based on weather data, and, optionally, a user's personal context information. In the example embodiment, server 110 contains a designated website for authorized users to access and use weather-based health program 112 and its associated databases on database server 140, via user device 130. In another embodiment, weather-based health program 112 may be distributed as a standalone computer program that can be executed directly on user device 130.

In an embodiment of the present invention, weather-based health program 112 includes programming instructions to scan a set of unstructured documents to identify one or more descriptors. The descriptors may include weather condition descriptors, adverse event descriptors, medical condition descriptors, and precautionary measure descriptors. A weather condition descriptor includes a span of electronic text characters associated with an atmospheric condition. An adverse event descriptor comprises a span of electronic text characters associated with an occurrence. A precautionary measure descriptor includes a span of electronic text characters associated with an action relative to the adverse event descriptor.

Scanning a set of unstructured documents includes receiving unstructured documents via an I/O device and performing natural language processing on the unstructured data (e.g. parsing) containing natural language text, or a span of electronic text characters. The natural language processing techniques may be employed by detectors and annotators known to one of ordinary skill in the art to identify a span of natural language text as either a weather condition descriptor or an adverse event descriptor.

With continued reference to FIG. 1, the functional modules of weather-based health program 112 include relationship extractor 114, data object generator 116, relationship instances retriever 118, relationship instances filter 120, and precautionary measures generator 122.

Relationship extractor 114 includes a set of programming instructions in weather-based health program 112. The set of programming instructions is executable by processor 128.

Relationship extractor 114 extracts relationships between descriptors stored in one or more lists of weather condition descriptors and adverse event descriptors. Accordingly, relationship extractor 114 receives as input one or more sets of descriptors (which may be entirely, or partially, in unstructured natural language form) stored in one or more lists of weather condition descriptors and adverse event descriptors. An adverse event descriptor may be an adverse medical event descriptor. An adverse event descriptor contains a span of electronic text that includes a verb in gerund form and a noun to which the verb applies, where the noun has a negative sentiment as determined by a sentiment analyzer.

Unstructured data refers to information that is not structured according to a predefined data model, or organized in a pre-defined manner. In the exemplary embodiment, lists database 141 may contain a list of identified words or phrases, from various sources of unstructured data, where each identified word or phrase is associated with either a weather condition <W>, an adverse event <E>, a medical condition <M>, or a precautionary measure <P>. These identified words or phrases are referred to as descriptors and, in the exemplary embodiment, are stored as one or more lists (i.e., weather condition descriptors, adverse event descriptors, medical condition descriptors, and precautionary measures descriptors) in lists database 141. In other embodiments, the various descriptors may be stored in any other fashion that enables access and dissemination by weather-based health program 112.

Relationship extractor 114 loads weather descriptor data and adverse event descriptor data from lists database 141, as described above. Relationship extractor 114 applies one or more relationship extraction methods to the descriptor data in lists database 141 to identify whether they are related, and optionally, to what extent they are related (e.g., measured as a scale of relatedness). The one or more relationship extraction methods may include a co-occurrence method, a machine learning method, a syntactic analysis method, or any other relationship extraction method known to one of ordinary skill in the art.

Co-occurrence is a linguistics term that can mean the above-chance frequent occurrence of two terms from a text corpus alongside each other in a certain order. For example, if the terms "hot" and "dehydration" occur within the same sentence in a majority of scanned unstructured data sources, then relationship extractor 114 may denote the descriptors, or terms, "hot" and "dehydration" as being related.

Machine learning is known in the art as a method to devise complex models and algorithms that can learn from and make predictions on data where the algorithms overcome following strictly static program instructions by making data driven predictions or decisions through building a model from sample inputs. In the example embodiment, relationship extractor 114 may have program instructions to predict relationships between weather condition descriptors and adverse event descriptors based on previous learned relationships and continued learning.

Syntactic analysis, or parsing, is the process of analyzing a string of symbols either in natural language, or computer languages, conforming to the rules of a formal grammar. Syntactic analysis is often performed in the art as a method of understanding the exact meaning of a sentence or word. Relationship extractor 114 may use syntactic analysis to determine dependency relations between a specific weather condition and its corresponding adverse event within a given source of weather data. For example, a scorching hot temperature may cause dehydration, or an extremely cold temperature may cause frostbite.

Relationship extractor 114 may measure relatedness between descriptors based on a Boolean determination, or a scalar determination. Obtaining a measure of relatedness between a weather condition descriptor and an adverse event descriptor, for example, enables relationship extractor 114 to store a level of confidence associated with the derived relationship. The level of confidence associated with the derived relationship may be used to rank, or weigh, the relationships between the identified descriptors. For example, if the descriptor "extreme cold" is found within the same paragraph as the descriptor "frostbite" in excess of a predefined threshold number of instances of unstructured data sources composed by different authors, then the relationship between "extreme cold" and "frostbite" may be assigned a higher value than a relationship between "extreme cold" and "cornea freeze", which are not identified within the same paragraph in excess of a predefined threshold number of instances.

The output of relationship extractor 114 is information that identifies descriptors and their relationships. For example, a first weather condition descriptor (i.e. extremely hot) is identified as being related to a first adverse event descriptor (i.e. dehydration), or a medical condition descriptor (i.e. diabetic) is identified as being related to a first precautionary measure descriptor (i.e. eat food high in sugar).

Data object generator 116 includes a set of programming instructions in weather-based health program 112 and operates via processor 128. Data object generator 116 generates a data object according to a data model based on the extracted relationships between the descriptors. A data model is a representation (or blueprint) that organizes data elements and standardizes how they relate to one another and to properties of entities that the data elements represent. In the exemplary embodiment, a data object may relate that the weather condition descriptor "hot" is related to the adverse event descriptor "dehydration", as derived from relationship extractor 114, by representing such model in metatags as $<W_1, E_{50}>$. W represents "weather condition descriptor" and E represents "adverse events descriptor". The subscript 1 associated with the W dictates that the word "hot" is the first word in a stored list of weather condition descriptors in lists database 141. The subscript 50 associated with the E dictates that the word "dehydration" is the $50^{th}$ word in a stored list of adverse event condition descriptors in lists database 141. The combination of $W_1$ and $E_{50}$ separated by a comma and encased within metatags represents a data object, or a recognized relationship between the two descriptors, as determined by relationship extractor 114.

Data object generator 116 creates, or builds, databases to store its generated data objects. The various databases depicted on database server 140 in FIG. 1 store the generated data objects based on the various combinations of descriptors, as described above and below. In the exemplary embodiment, data object generator 116 builds the various databases by generating data objects that include the following relationships, as determined by relationship extractor 114: $<W_{number}, E_{number}>$, $<W_{number}, E_{number}, M_{number}>$, $<W_{number}, E_{number}, P_{number}>$, and $<W_{number}, E_{number}, P_{number}, M_{number}>$; wherein M represents medical condition descriptors, P represents precautionary measures descriptors, and $_{number}$ represents the identified descriptor's numerical spot within the stored list of either W, E, M, or Ps in lists database 141.

According to an embodiment, data object generator 116 generates a data object having at least three descriptors. The at least three descriptors may include <W>, <E>, and <M> descriptors. The medical condition descriptor <M> includes a span of electronic text characters associated with an illness or abnormality. The descriptors in a generated data object are deemed related to one another by having a corresponding relationship as determined by relationship extractor 114. The <W,E,M> data object is stored in relationships database 144.

According to an embodiment, data object generator 116 generates a data object having at least four descriptors. The at least four descriptors may include <W>, <E>, <M>, and <P> descriptors. The descriptors in a generated data object are deemed related to one another by having a corresponding relationship as determined by relationship extractor 114. The <W,E,M,P> data object is stored in relationships database 148.

Relationship instances retriever 118 is a set of programming instructions in weather-based health program 112 and operates via processor 128. Relationship instances retriever 118 retrieves a set of candidate unstructured documents comprising instances of an adverse event descriptor and a related weather condition descriptor. In the exemplary embodiment, candidate unstructured documents refer to the online and offline journal articles, blogs, discussions, corpora of data, personal health records, weather databases, medical encyclopedias, peer-reviewed data journals, online data and the like, that contain identified relationships between weather conditions descriptors and adverse events descriptors as determined by relationship extractor 114, and stored as data objects in relationships databases 142.

In an optional embodiment of the present invention, candidate unstructured documents may comprise instances of adverse events descriptors, related weather conditions descriptors, and further related medical conditions descriptors as determined by relationship extractor 114, and stored as data objects in relationships database 144. For example, if relationship instances retriever 118 retrieves a set of candidate unstructured documents that contain the data object $<W_1, E_{50}>$, which identifies the relationship between hot weather and dehydration, then the program may further scan the set of candidate documents to further identify corresponding precautionary measures descriptors associated with hot weather and dehydration. Likewise, if relationship instances retriever 118 retrieves a set of candidate documents that contain data objects (i.e. $<W_{number}, E_{number}>$ or $<W_{number}, E_{number}, M_{number}>$), as identified in relationships database 142 or 144, identifying "freezing cold temperature" with "freezing corneas" and "diabetes", then the program may further scan the set of candidate documents for precautionary measures descriptors associated with the specific data object at hand.

Relationship instances filter 120 includes a set of programming instructions in weather-based health program 112 and operates via processor 128. Relationship instances filter 120 filters the retrieved set of candidate unstructured documents by selecting candidate unstructured documents that comprise a precautionary measure descriptor. In the exemplary embodiment, relationship instances filter 120 filters the retrieved set of candidate unstructured documents based on whether the particular document includes a precautionary measures descriptor, as listed in lists database 141, represented by $<P_{number}>$. If, for example, the candidate document contains a precautionary measure descriptor, then that document may be one of many selected to create a summary of precautionary measures for each identified adverse event. If the candidate document does not contain a precautionary measure descriptor, then that particular document may be filtered out. In another embodiment, the presence or absence of words within the candidate document that indicate a precautionary measure such as "precaution", "measure", and the like, determine whether a particular candidate document is selected to create a summary of precautionary measures for each identified adverse event. The precautionary measure descriptor <P> associated with an adverse event descriptor <E> and its related weather condition descriptor <W> is stored as a data object in relationships database 146 as <$W_{number}$, $E_{number}$, $P_{number}$>.

In a further embodiment, relationship instances filter 120 selects candidate unstructured documents that includes a relationship rule between a weather condition descriptor and an adverse event descriptor. A relationship rule between a <W> and an <E>, for example, may advise to take certain "precautions" in <$W_{10}$>, wherein lists database 141 identifies <$W_{10}$> as rainy weather. Another relationship rule within a retrieved candidate document may be, "advice to avoid" <$E_{122}$> during <$W_{88}$>, wherein <$E_{122}$> is "struck by lightning" and <$W_{88}$> is "lightning storms". The specific "precautions" and "advice to avoid", associated with <$W_{number}$, $E_{number}$> or, optionally <$W_{number}$, $E_{number}$, $M_{number}$>, within the set of candidate unstructured documents generates a new data object stored in relationships database 146 as <$W_{number}$, $E_{number}$, $P_{number}$> or relationships database 148 as <$W_{number}$, $E_{number}$, $M_{number}$, $P_{number}$> wherein P identifies a word or phrase associated with a precautionary measure descriptor as listed in lists database 141.

In an alternative embodiment, relationship instances filter 120 may select candidate unstructured documents that include a <$W_{number}$, $E_{number}$> data object, and further apply a rule that examines the subject, verb, noun sentence structure within the candidate unstructured document in order to detect relationships. For example, relationship instances filter 120 may determine that the subject of the sentence contains a <W> in lists database 141, an <E> in lists database 141, and a verb that denotes causation between the <W> and <E>, such as "causes" or "results from", and the like.

According to an embodiment, relationship instances filter 120 filters the relationships that relationship extractor 114 generates. Relationship instances filter 120 generates a candidate data object that includes descriptors identified as related. For example, it considers as a candidate data object <$W_1,E_5$>, which relationship extractor 114 has identified as being related. Relationship instances filter 120 presents the candidate data object to a user for identification of known relationships. Relationship instances filter 120 receives an input from the user identifying the candidate data object as including descriptors having a known relationship. In the example embodiment, relationship instances filter 120 filters, from the relationships that relationship extractor 114 generated, the candidate data the user-identified candidate data object. The user-identified candidate data object includes descriptors that have a known relationship, according to the user. Based on the filtering, the data object that data object generator 116 generates excludes the filtered candidate data object.

In various instances of filtering a retrieved set of candidate documents, relationship instances filter 120 may include a set of precautionary measures that do not bear much relevance to a user. For example, relationship instances filter 120 may include in its summary of precautionary measures to "dress warm <P>" when determining that "the flu <E>" is an adverse event that may result from "cold weather <W>". An average person may already realize that it is advisable to dress warm when it is cold outside, in order to avoid catching the flu. To circumvent the inclusion of already known, or related, precautionary measures for a particular weather condition, relationship instances filter 120 filters the retrieved set of candidate unstructured documents, in a further embodiment, based on human testers flagging a candidate set of extracted relationships between weather condition descriptors, adverse event descriptors, and precautionary measures descriptors as being "known" or "unknown". The relationships that are flagged as "unknown", greater than a pre-defined threshold, are selected for use in relationships database 146 and 148. The relationships that are flagged as "known", greater than a pre-defined threshold, are filtered out. For example, an average person may already know to "take an umbrella" <P> when it's "raining" <W> in order to avoid "getting wet" <E>.

Precautionary measures generator 122 includes a set of programming instructions in weather-based health program 112 and operates via processor 128. Precautionary measures generator 122 generates a summary of unstructured text comprising precautionary measure information associated with the precautionary measure descriptor. The generated summary of unstructured text expands on the precautionary measure descriptor contained in lists database 141. For example, precautionary measures generator may generate a summarized precautionary measure as follows: "Abstain from shoveling snow. If you must, scoop fresh, not packed snow. Push, rather than lift, and fill the shovel to only half full or less. Stop when the exertion feels more than 'somewhat difficult'". Summarization techniques may include those already known to one of ordinary skill in the art.

In the example embodiment, user device 130 contains user interface 132, and location detector 134. User interface 132 is a computer program which allows a user to interact with user device 130 and other connected devices via network 150. For example, user interface 132 may be a graphical user interface (GUI). In addition to comprising a computer program, user interface 132 may be connectively coupled to hardware components, such as those depicted in FIG. 3, for receiving user input. In the example embodiment, user interface 132 is a web browser, however in other embodiments, user interface 132 may be a different program capable of receiving user interaction and communicating with other devices.

In the example embodiment, location detector 134 (software or hardware and software combination) is a computer program on user device 130 which communicates with a global positioning system (GPS) to provide time and location information. Modern GPS systems operate on the concept of time and location. In modern GPS systems, four or more satellites broadcast a continuous signal detailing satellite identification information, time of transmission (TOT), and the precise location of the satellite at the time of transmission. When a GPS receiver, such as location detector 134, picks up the signal, location detector 134 determines the difference in time between the time of transmission (TOT) and the time of arrival (TOA) at location detector 134. Based on the amount of time it took to receive the signals and the precise locations of the satellites when the signals were sent, GPS receivers are capable of determining the location where the signals were received. In the example embodiment, location detector 134 provides real-time weather conditions or any other input from external service providers.

In various embodiments, user device 130 may be a laptop computer, tablet computer, netbook computer, personal computer (PC), a desktop computer, a personal digital assistant (PDA), a smart phone, or any programmable electronic device capable of communicating with server 110 and database server 140 via network 150. User device 130 may include internal and external hardware components, as depicted and described in further detail below with reference to FIG. 3. In other embodiments, user device 130 may be implemented in a cloud computing environment, as described in relation to FIGS. 4 and 5, herein.

According to an embodiment, user device 130 may be a wearable device such as a health and wellness tracker in wristwatch form. User device 130 may be equipped with one or more biometric sensors and it may be in contact with various databases containing medical records of the user wearing user device 130. User device 130 may also have wireless connectivity capabilities allowing it to communicate with server 110, database server 140, and other computers or servers over network 150.

According to an embodiment of the invention, weather-based health program 112 receives a weather condition descriptor associated with a user. The weather condition descriptor may be received in the form of an electronic signal from user device 130 (for example, the user may enter specific weather condition descriptors into user device 130), or from another data source such as a weather database or application in real-time.

Weather-based health program 112 queries the relationships databases stored on database server 140 to determine a corresponding adverse event descriptor and a precautionary measure descriptor associated with the received weather descriptor. Weather-based health program 112 generates a message to the user, via user device 130, based on the adverse event descriptors and related precautionary measure descriptors. The related precautionary measure descriptors are summarized using any known natural language processing methods in the art. The generated message to the user is based on the summarized precautionary measure descriptors.

In presenting messages to the user about what precautions the user should take given one or more weather conditions that the user is experiencing, or is expected to experience, weather-based health program 112 may communicate to user device 130 those precautionary measures descriptor summaries that are most relevant to the user's known or discoverable medical conditions. For example, where user device 130 is a wearable device, detecting that the user is experiencing heart palpitations may make a difference in the precautionary measures that the user should receive compared to another user with a regular heartbeat, even though both might experience the same weather conditions.

Additionally, a single user may suffer from multiple medical conditions that are likely to result in one or more adverse medical events given a current, or expected, weather condition. Furthermore, these adverse medical events that are likely to occur may, for the most part, be unexpected by the user; such that the user would benefit from receiving messages alerting the user to take precautions. However, the user may be overwhelmed if too many precautionary measures are provided. One solution is to expand on the functionality of user-feedback filtering. Where filtering is used to identify "known" versus "unknown" relationships between weather condition descriptors and adverse event descriptors (and adverse medical event descriptors) via user feedback; the filtering may be extended to measure how "known" versus how "unknown" these relationships are. For example, multiple users may be prompted for feedback, and their feedback as to relationships may be captured in a score. A relationship identified as "known" by 10 users may have a score of 1 (relatively well-known), whereas a relationship identified as "known" by only two users may have a score of 0.2 (relatively unknown). In providing messages of precautionary measures to user device 130, weather-based health program 112 may limit its communications to the least-known relationships and their corresponding precautionary measures, based on the scores.

According to an embodiment, the generated data object includes at least four descriptors, including a weather condition descriptor, an adverse event descriptor, a medical condition descriptor, and a precautionary measure descriptor, where the at least four descriptors have a corresponding extracted relationship, and where the determining further includes receiving a medical condition descriptor associated with the user, and where generating the message is further based on the received medical condition descriptor.

According to an embodiment, weather-based health program 112 receives a medical condition descriptor of the user and scores previously generated data objects based on the received medical condition descriptor of the user.

In the example embodiment, network 150 is a communication channel capable of transferring data between connected devices and may be a telecommunications network used to facilitate telephone calls between two or more parties comprising a landline network, a wireless network, a closed network, a satellite network, or any combination thereof. In another embodiment, network 150 may be the Internet, representing a worldwide collection of networks and gateways to support communications between devices connected to the Internet. In this other embodiment, network 150 may include, for example, wired, wireless, or fiber optic connections which may be implemented as an intranet network, a local area network (LAN), a wide area network (WAN), or any combination thereof. In further embodiments, network 150 may be a Bluetooth network, a WiFi network, or a combination thereof. In general, network 150 can be any combination of connections and protocols that will support communications between user device 130, server 110, and database server 140.

Figure 2A:
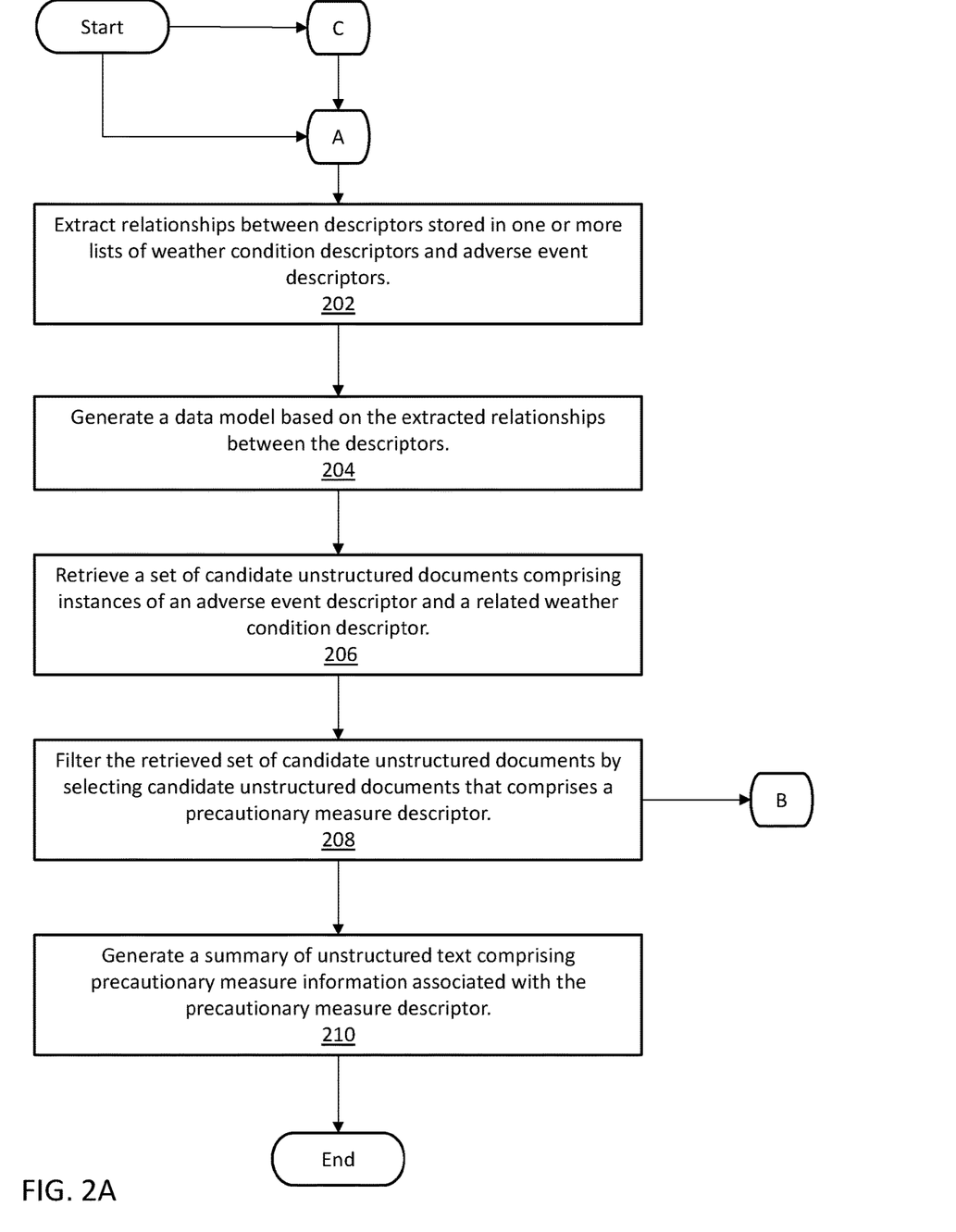
FIGS. 2A, 2B, and 2C are flowcharts illustrating the operation of a weather-based health program of FIG. 1, in accordance with embodiments of the present invention.
Figure 2B:
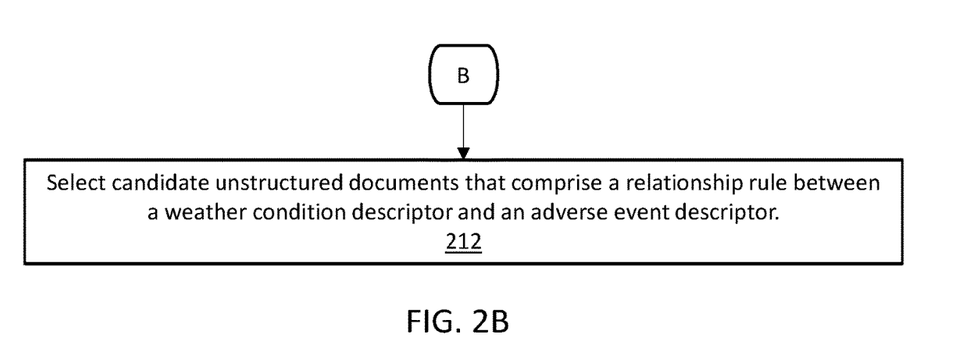
Figure 2C:
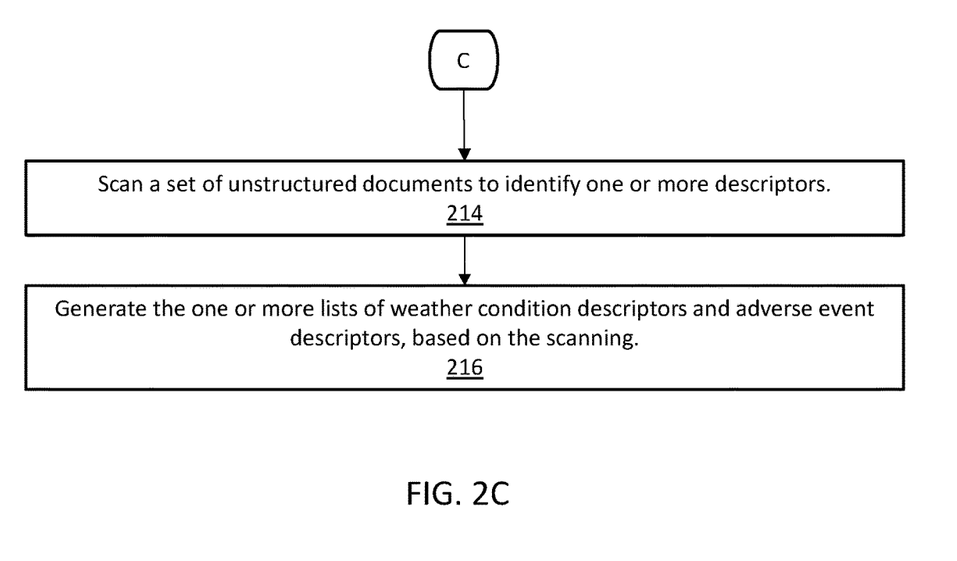

FIGS. 2A-2C are flowcharts depicting operational steps of a method for performing electronic natural language processing on unstructured data, according to an embodiment of the present invention. The method of FIG. 2C is discussed further in reference to an illustrative example.

Referring now to FIGS. 1 and 2C, weather-based health program 112 scans a set of unstructured documents to identify one or more descriptors (step 214). Descriptors refer to words or phrases within an unstructured text document that refer to either a weather condition <W>, an adverse event <E>, a medical condition <M>, or a precautionary measure <P>. A weather condition descriptor includes a span of electronic text characters associated with an atmospheric condition. An adverse event descriptor includes a span of electronic text characters associated with an occurrence, and a precautionary measure descriptor includes a span of electronic text characters associated with an action relative to the adverse event descriptor. For example, weather-based health program 112 scans an online medical journal article and identifies "cold weather" as a <W>, "heart attack" as an <E>, "heart palpitations" as an <M>, and "do not ingest alcohol if you plan to go outside" as a <P>.

With continued reference to FIGS. 1 and 2C, weather-based health program 112 generates one or more lists of weather condition descriptors and adverse event descriptors, based on the scanning (step 216). The identified descriptors are stored in lists database 141 according to whether they are weather condition descriptors <W>, adverse event descriptors <E>, medical condition descriptors <M>, or precautionary measure descriptors <P>, wherein each <W>, <E>, <M>, and <P> list may contain various descriptor words or phrases as denoted by a subscript, such as <$W_5$> which indicates that this particular descriptor word or phrase is listed fifth in the list of weather condition descriptors.

Referring now to FIGS. 1 and 2A, relationship extractor 114, via processor 128, extracts relationships between descriptors stored in one or more lists of weather condition descriptors and adverse event descriptors (step 202). For example, relationship extractor 114 determines that "cold weather" <$W_1$> is related to "increased chance of heart attack" <$E_5$> by running a co-occurrence analysis on a set of medical literature documents containing unstructured natural language text, and determining that the two descriptors in question occur according to the specific co-occurrence pattern rule under use (for example, they are often found in the same sentence in multiple documents). Relationship extractor 114 therefore identifies these two descriptors as related.

According to an embodiment, weather-based health program 112 extracts relationships between descriptors stored in one or more lists of weather condition descriptors and adverse event descriptors by identifying the relationships using any one or more of: a co-occurrence analysis process, a machine learning process, and a syntactic analysis process.

Data object generator 116, via processor 128, generates a data object according to a data model based on the extracted relationships between the descriptors (step 204). For example, if cold weather increases chances of a heart attack, then data object generator 116 generates the following data object that appears as follows <$W_1$, $E_5$>, and is stored in relationships database 142.

Optionally, relationship extractor 114 may generate a data object comprising at least three descriptors, including a weather condition descriptor, an adverse event descriptor, and a medical condition descriptor, where the at least three descriptors have a corresponding extracted relationship, and where a medical condition descriptor comprises a span of electronic text characters associated with an illness or abnormality. For example, data object generator 116 may determine that "heart palpitations", a medical condition descriptor, is related to <$W_1$, $E_5$> by running a co-occurrence analysis on the set of medical literature documents and determine that the descriptors occur according to a specific co-occurrence pattern rule under use (for example, they are found in the same paragraph in multiple documents). As such, data object generator 116 generates a data object according a data model based on the extracted relationships between <$W_1$, $E_5$, $M_{23}$>, where "heart palpitations" is listed in lists database 141 as the $23^{rd}$ medical condition descriptor in the list.

In another embodiment, data object generator 116 generates a data object comprising at least four descriptors, including a weather condition descriptor, an adverse event descriptor, a medical condition descriptor, and a precautionary measure descriptor, wherein the at least four descriptors have a corresponding extracted relationship. For example, a data object comprising at least four descriptors may include a <P> descriptor and appear as <$W_1$, $E_5$, $M_{23}$, $P_{33}$>, where "avoid cold weather conditions" is listed in lists database 141 as the $33^{rd}$ precautionary measure descriptor in the list.

Relationship instances retriever 118, via processor 128, retrieves a set of candidate unstructured documents that comprise instances of an adverse event descriptor and a related weather condition descriptor (step 206). For example, relationship instances retriever 118 retrieves a set of medical literature documents containing <$W_1$, $E_5$> in order to apply natural language processing rules to find precautionary measure descriptors associated with <$W_1$, $E_5$>.

Relationship instances filter 120, via processor 128, filters the retrieved set of candidate unstructured documents by selecting candidate unstructured documents that comprises a precautionary measure descriptor (step 208). For example, relationship instances filter 120 applies natural language processing rules to identify the presence or absence of precautionary measure descriptor words or phrases, as contained in lists database 141. If, for example, the candidate unstructured document contains the precautionary measure descriptor "do not ingest alcohol if you plan to go outside", then the candidate document is selected because it contains a precautionary measure descriptor. If the candidate unstructured document does not contain a precautionary measure descriptor within the text, then it is filtered out.

Referring now to FIGS. 1 and 2B, relationship instances filter 120, via processor 128, selects candidate unstructured documents that comprise a relationship rule between a weather condition descriptor and an adverse event descriptor (step 212). Relationship instances filter 120 may be configured to detect certain relationship rules between a <W> and an <E> in order to determine the presence or absence of a <P> within the candidate document. For example, a relationship rule may include identifying the <E> and <W> preceded by or separated by one or two non-descriptor words in the text, such as "precautions in <W>", or "advice to avoid <E> during <W>". If relationship instances filter 120 identifies a given relationship rule within the candidate document, then it is selected for use since it contains precautionary measure descriptors. If relationship instances filter 120 does not identify a given relationship rule within the candidate document, then it is filtered out.

Referring again to FIGS. 1 and 2A, precautionary measures generator 122, via processor 128, generates a summary of unstructured text comprising precautionary measure information associated with the precautionary measure descriptor (step 210). Precautionary measures generator 122 generates a summary that expands on the precautionary measure descriptor <P>, stored in lists database 141, by utilizing a summarization technique known to one of ordinary skill in the art. For example, precautionary measures generator 122 expands on <$P_{123}$>, which contains the phrase "no sudden exertion", and is associated with the generated data object <$W_1$, $E_5$>, by outputting the following summary: "Abstain from shoveling snow. If you must, scoop fresh, not packed snow. Push, rather than lift, and fill the shovel to only half full or less. Stop when the exertion feels more than somewhat difficult."

Referring now generally to FIGS. 1 and 2A-C, relationship instances filter 120 filters the relationships that relationship extractor 114 generates. Relationship instances filter 120 generates a candidate data object that includes descriptors identified as related. For example, it considers as a candidate data object <$W_1$,$E_5$>, which relationship extractor 114 has identified as being related. Relationship instances filter 120 presents the candidate data object to a user for identification of known relationships. Relationship instances filter 120 receives an input from the user identifying the candidate data object as including descriptors having a known relationship. In the example embodiment, relationship instances filter 120 filters, from the relationships that relationship extractor 114 generated, the candidate data the user-identified candidate data object. The user-identified candidate data object includes descriptors that have a known relationship, according to the user. Based on the filtering, the data object that data object generator 116 generates excludes the filtered candidate data object.

According to an embodiment, weather-based health program 112 receives a weather descriptor associated with a user and queries the relationships databases stored on database server 140 to determine a corresponding adverse event descriptor and a precautionary measure descriptor associated with the received weather descriptor. Weather-based health program 112 generates a message to the user, via user device 130, based on the corresponding adverse event descriptors and related precautionary measure descriptors. The related precautionary measure descriptors are summarized using any known natural language processing methods in the art. The generated message to the user is based on the summarized precautionary measure descriptors.

According to an embodiment, the generated data object includes at least four descriptors, including a weather condition descriptor, an adverse event descriptor, a medical condition descriptor, and a precautionary measure descriptor, where the at least four descriptors have a corresponding extracted relationship, and where the determining further includes receiving a medical condition descriptor associated with the user, and where the generation of the message is further based on the received medical condition descriptor.

According to an embodiment, weather-based health program 112 receives a medical condition descriptor of the user and scores data objects previously generated based on the received medical condition descriptor of the user.

Referring now generally to embodiments of the invention, a method for performing electronic natural language processing on unstructured data may be performed by one or more of the following functions.

Figure 3:
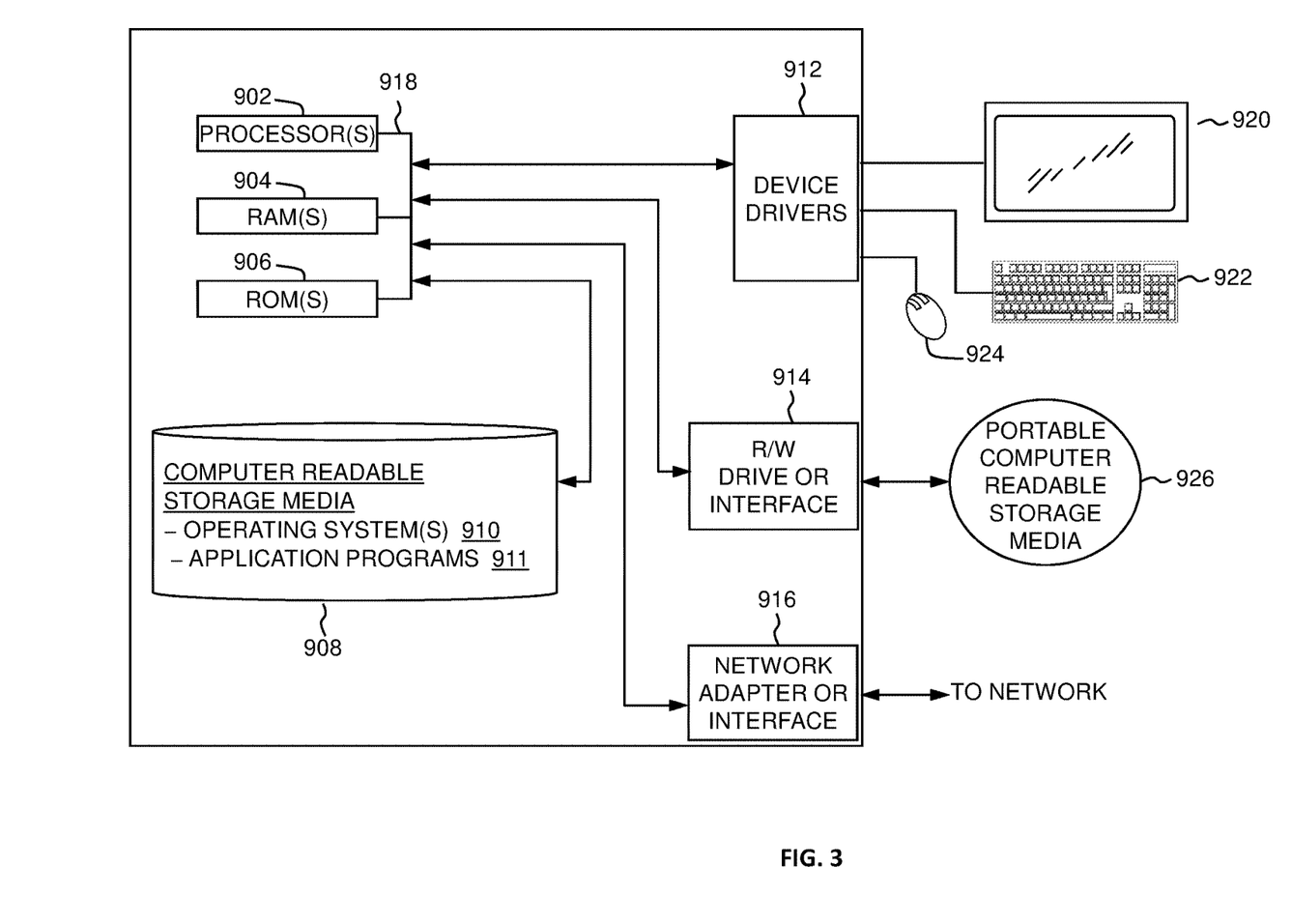
FIG. 3 is a diagram graphically illustrating the hardware components of the computing environment of FIG. 1, in accordance with an embodiment of the present invention.

FIG. 3 is a block diagram depicting components of a computing device (such as server 110, database server 140, or user device 130, as shown in FIG. 1), in accordance with an embodiment of the present invention. It should be appreciated that FIG. 3 provides only an illustration of one implementation and does not imply any limitations with regard to the environments in which different embodiments may be implemented. Many modifications to the depicted environment may be made.

User device 130 may include one or more processors 902, one or more computer-readable RAMs 904, one or more computer-readable ROMs 906, one or more computer readable storage media 908, device drivers 912, read/write drive or interface 914, network adapter or interface 916, all interconnected over a communications fabric 918. Communications fabric 918 may be implemented with any architecture designed for passing data and/or control information between processors (such as microprocessors, communications and network processors, etc.), system memory, peripheral devices, and any other hardware components within a system.

One or more operating systems 910, and one or more application programs 911, such as weather-based health program 112, may be stored on one or more of the computer readable storage media 908 for execution by one or more of the processors 902 via one or more of the respective RAMs 904 (which typically include cache memory). In the illustrated embodiment, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

User device 130 may also include a R/W drive or interface 914 to read from and write to one or more portable computer readable storage media 926. Application programs 911 on user device 130 may be stored on one or more of the portable computer readable storage media 926, read via the respective R/W drive or interface 914 and loaded into the respective computer readable storage media 908.

User device 130 may also include a network adapter or interface 916, such as a TCP/IP adapter card or wireless communication adapter (such as a 4G wireless communication adapter using OFDMA technology). Application programs 911 on user device 130 may be downloaded to the computing device from an external computer or external storage device via a network (for example, the Internet, a local area network or other wide area network or wireless network) and network adapter or interface 916. From the network adapter or interface 916, the programs may be loaded onto computer readable storage media 908. The network may comprise copper wires, optical fibers, wireless transmission, routers, firewalls, switches, gateway computers and/or edge servers.

User device 130 may also include a display screen 920, a keyboard or keypad 922, and a computer mouse or touchpad 924. Device drivers 912 interface to display screen 920 for imaging, to keyboard or keypad 922, to computer mouse or touchpad 924, and/or to display screen 920 for pressure sensing of alphanumeric character entry and user selections. The device drivers 912, R/W drive or interface 914 and network adapter or interface 916 may comprise hardware and software (stored on computer readable storage media 908 and/or ROM 906).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Figure 4:
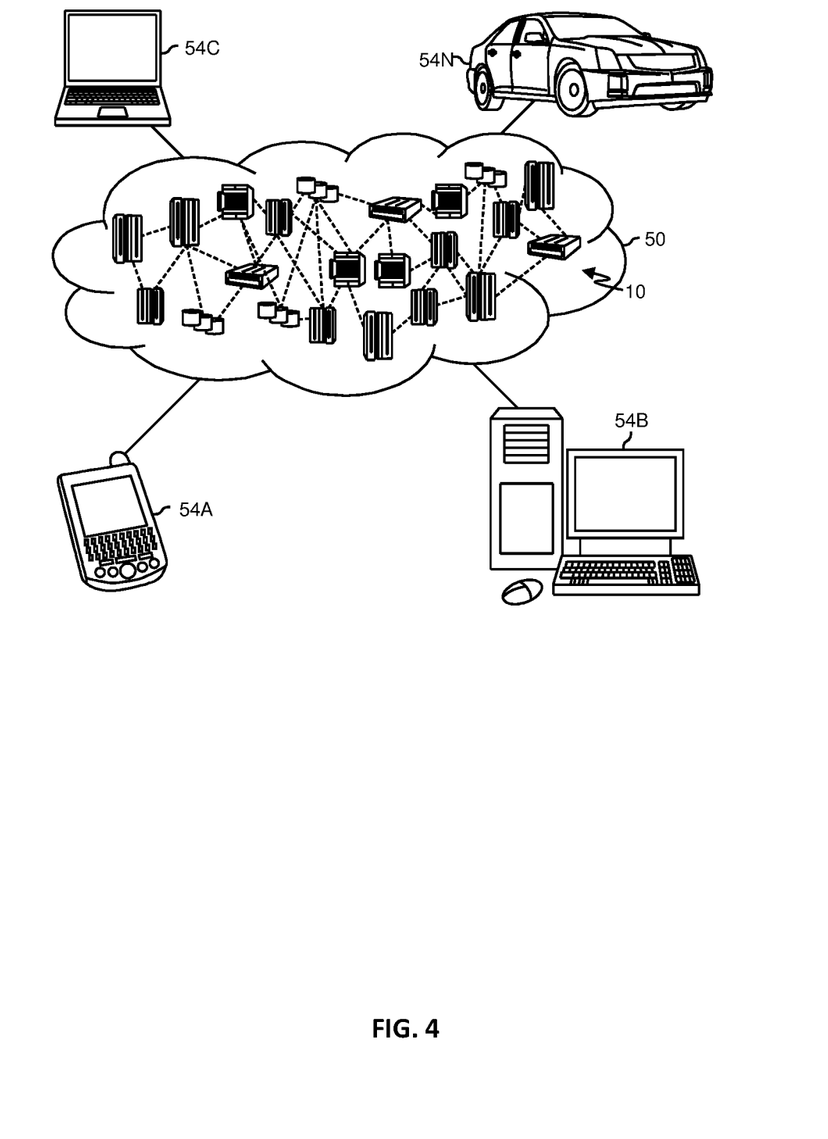
FIG. 4 depicts a cloud computing environment, in accordance with an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
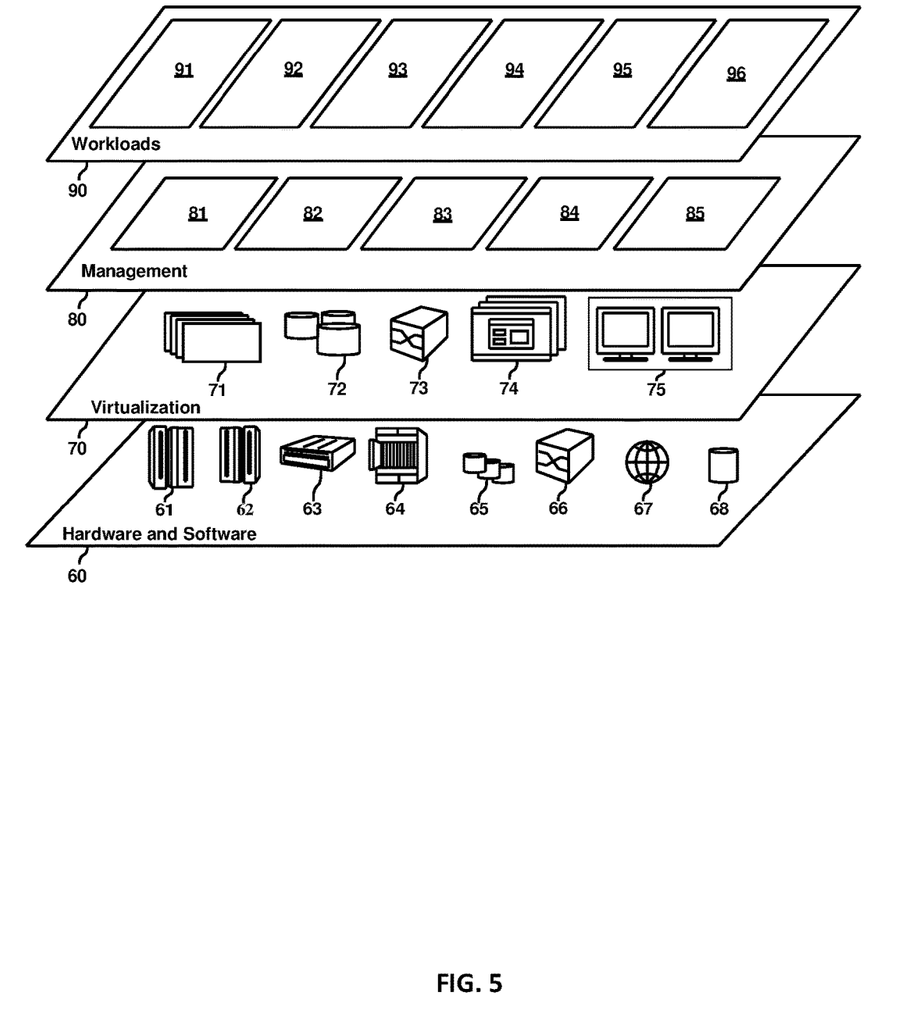
FIG. 5 depicts abstraction model layers of the illustrative cloud computing environment of FIG. 4, in accordance with an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and electronic natural language processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Based on the foregoing, a computer system, method, and computer program product have been disclosed. However, numerous modifications and substitutions can be made without deviating from the scope of the present invention. Therefore, the present invention has been disclosed by way of example and not limitation.

The invention claimed is:

1. A method for performing electronic natural language processing on unstructured data, comprising:
    extracting relationships between descriptors stored in one or more lists of weather condition descriptors and adverse event descriptors;
    generating a data object according to a data model, based on the extracted relationships between the descriptors, wherein generating the data object according to the data model further comprises generating the data object comprising at least three descriptors, including a weather condition descriptor, an adverse event descriptor, and a medical condition descriptor, wherein the at least three descriptors have a corresponding extracted relationship, and wherein the medical condition descriptor comprises a span of electronic text characters associated with an illness or abnormality;
    retrieving a set of candidate unstructured documents comprising instances of the adverse event descriptor and a related weather condition descriptor;
    filtering the retrieved set of candidate unstructured documents by selecting candidate unstructured documents that comprise a precautionary measure descriptor; and
    displaying the filtered set of candidate unstructured documents on a display device.

2. The method of claim 1, wherein the filtering further comprises:
    selecting candidate unstructured documents that comprise a relationship rule between the weather condition descriptor and the adverse event descriptor.

3. The method of claim 1, further comprising:
    generating a summary of unstructured text comprising precautionary measure information associated with the precautionary measure descriptor.

4. The method of claim 1, further comprising:
    scanning a set of unstructured documents to identify one or more descriptors; and
    generating the one or more lists of weather condition descriptors and adverse event descriptors based on the scanning.

5. The method of claim 1,
    wherein the weather condition descriptor comprises a span of electronic text characters associated with an atmospheric condition,
    wherein the adverse event descriptor comprises a span of electronic text characters associated with an occurrence, and
    wherein the precautionary measure descriptor comprises a span of electronic text characters associated with an action relative to the adverse event descriptor.

6. The method of claim 1, wherein generating a data object according to the data model further comprises:
    generating the data object to include at least four descriptors, including the weather condition descriptor, the adverse event descriptor, the medical condition descriptor, and the precautionary measure descriptor, wherein the at least four descriptors have the corresponding extracted relationship.

7. The method of claim 1, wherein extracting the relationships between descriptors stored in the one or more lists of weather condition descriptors and adverse event descriptors comprises:
    generating a candidate data object comprising descriptors identified as related;
    presenting the candidate data object to a user for identification of known relationships;
    receiving an input from the user identifying the candidate data object as comprising the descriptors having a known relationship; and
    filtering from the extracted relationships the user-identified candidate data object comprising descriptors having a known relationship, wherein generating a data object according to a data model excludes the filtered candidate data object.

8. The method of claim 1, further comprising:
    receiving the weather condition descriptor associated with a user;
    determining, based on the generated data object, the adverse event descriptor and the precautionary measure descriptor associated with the received weather condition descriptor; and
    generating a message to the user based on the adverse event descriptor and a related precautionary measure descriptor.

9. The method of claim 8, wherein generating a message to the user comprises:
    generating the message based on a summary of the related precautionary measure descriptor.

10. The method of claim 8, wherein the generated data object comprises at least four descriptors, including a weather condition descriptor, an adverse event descriptor, a medical condition descriptor, and a precautionary measure descriptor, wherein the at least four descriptors have a corresponding extracted relationship, and wherein the determining further comprises:

receiving the medical condition descriptor associated with the user,
wherein generating the message is further based on the received medical condition descriptor.

11. The method of claim 8, further comprising:
receiving the medical condition descriptor of the user;
scoring data objects in the generated data model based on the received medical condition descriptor of the user.

12. The method of claim 1, wherein extracting relationships between descriptors stored in one or more lists of weather condition descriptors and adverse event descriptors comprises:
identifying the relationships using any one or more of: a co-occurrence analysis process, a machine learning process, and a syntactic analysis process.

13. The method of claim 1, wherein an adverse event descriptor comprises:
a span of electronic text that includes a verb in gerund form and a noun to which the verb applies, where the noun has a negative sentiment as determined by a sentiment analyzer.

14. A computer program product for performing electronic natural language processing on unstructured data, comprising a non-transitory tangible storage device having program code embodied therewith, the program code executable by a processor of a computer to perform a method, the method comprising:
extracting, by the processor, relationships between descriptors stored in one or more lists of weather condition descriptors and adverse event descriptors;
generating, by the processor, a data object according to a data model, based on the extracted relationships between the descriptors,
wherein generating, by the processor, the data object according to the data model further comprises generating, by the processor, the data object comprising at least three descriptors, including a weather condition descriptor, an adverse event descriptor, and a medical condition descriptor, wherein the at least three descriptors have a corresponding extracted relationship, and wherein the medical condition descriptor comprises a span of electronic text characters associated with an illness or abnormality;
retrieving, by the processor, a set of candidate unstructured documents comprising instances of the adverse event descriptor and a related weather condition descriptor;
filtering, by the processor, the retrieved set of candidate unstructured documents by selecting candidate unstructured documents that comprise a precautionary measure descriptor; and
displaying, by the processor, the filtered set of candidate unstructured documents on a display device.

15. The computer program product of claim 14, wherein the method further comprises:

generating, by the processor, a summary of unstructured text comprising precautionary measure information associated with the precautionary measure descriptor.

16. The computer program product of claim 14, wherein the method further comprises:
scanning, by the processor, a set of unstructured documents to identify one or more descriptors; and
generating, by the processor, the one or more lists of weather condition descriptors and adverse event descriptors based on the scanning.

17. A computer system for performing electronic natural language processing on unstructured data, comprising:
one or more computer devices each having one or more processors and one or more tangible storage devices; and
a program embodied on at least one of the one or more storage devices, the program having a plurality of program instructions for execution by the one or more processors, the program instructions comprising instructions for:
extracting, by the computer, relationships between descriptors stored in one or more lists of weather condition descriptors and adverse event descriptors;
generating, by the computer, a data object according to a data model, based on the extracted relationships between the descriptors,
wherein generating, by the computer, the data object according to the data model further comprises generating, by the computer, the data object comprising at least three descriptors, including a weather condition descriptor, an adverse event descriptor, and a medical condition descriptor, wherein the at least three descriptors have a corresponding extracted relationship, and wherein the medical condition descriptor comprises a span of electronic text characters associated with an illness or abnormality;
retrieving, by the computer, a set of candidate unstructured documents comprising instances of the adverse event descriptor and a related weather condition descriptor;
filtering, by the computer, the retrieved set of candidate unstructured documents by selecting candidate unstructured documents that comprise a precautionary measure descriptor; and
displaying, by the computer, the filtered set of candidate unstructured documents on a display device.

18. The computer system of claim 17, wherein the program instructions further comprise instructions for:
generating, by the computer, a summary of unstructured text comprising precautionary measure information associated with the precautionary measure descriptor.

19. The computer system of claim 17, wherein the program instructions further comprise instructions for:
scanning, by the computer, a set of unstructured documents to identify one or more descriptors; and
generating, by the computer, the one or more lists of weather condition descriptors and adverse event descriptors based on the scanning.

* * * * *